United States Patent [19]
Kopf

[11] Patent Number: 6,139,746
[45] Date of Patent: Oct. 31, 2000

[54] METHOD AND APPARATUS FOR PURIFICATION OF BIOLOGICAL SUBSTANCES

[76] Inventor: Henry B. Kopf, 108 Coatbridge Cir., Cary, N.C. 27511

[21] Appl. No.: 09/300,891

[22] Filed: Apr. 28, 1999

Related U.S. Application Data

[63] Continuation-in-part of application No. 09/255,186, Feb. 22, 1999.

[51] Int. Cl.[7] .................................................. B01D 15/08
[52] U.S. Cl. ........................ 210/635; 210/651; 210/656; 210/659; 210/198.2; 530/413; 530/414; 530/417; 530/387.1
[58] Field of Search .................................... 210/635, 650, 210/651, 656, 659, 653, 654, 655, 198.2; 530/413, 414, 417, 387.1

[56] References Cited

U.S. PATENT DOCUMENTS

| | | | |
|---|---|---|---|
| 4,443,231 | 4/1984 | Siegell | 55/3 |
| 4,606,825 | 8/1986 | Crane et al. | 210/635 |
| 4,748,234 | 5/1988 | Dorin et al. | 530/412 |
| 4,867,876 | 9/1989 | Kopf | 210/228 |
| 4,877,866 | 10/1989 | Rudnick et al. | 530/387 |
| 4,882,050 | 11/1989 | Kopf | 210/231 |
| 5,034,124 | 7/1991 | Kopf | 210/231 |
| 5,049,268 | 9/1991 | Kopf | 210/231 |
| 5,077,391 | 12/1991 | Raison et al. | 530/387 |
| 5,118,796 | 6/1992 | Prior et al. | 530/388.1 |
| 5,177,194 | 1/1993 | Sarno et al. | 530/412 |
| 5,232,589 | 8/1993 | Kopf | 210/228 |
| 5,259,971 | 11/1993 | Smith Morse et al. | 210/650 |
| 5,342,517 | 8/1994 | Kopf | 210/228 |
| 5,593,580 | 1/1997 | Kopf | 210/321.75 |
| 5,868,930 | 2/1999 | Kopf | 210/321.75 |

*Primary Examiner*—Ernest G. Therkorn
*Attorney, Agent, or Firm*—Steven J. Hultquist; William A. Barrett

[57] ABSTRACT

A process and apparatus for purifying one or more target substances from a source liquid, employing one or more cross-flow filter elements, and one or more types of chromatography resins, in combination, to provide purification with advantageous yield, product purity, and cost -and time-efficiency.

62 Claims, 7 Drawing Sheets

METHOD AND APPARATUS FOR PURIFICATION OF BIOLOGICAL SUBSTANCES

This appln is a C-I-P of Ser. No. 09/255,186 filed Feb. 22, 1999.

BACKGROUND OF THE INVENTION

1. Field of the Invention

The invention relates generally to a method and apparatus for purifying target biological substance(s), such as selected proteins, antibodies, antigens, clotting factors, glycoproteins, and hormones, from source liquids containing contaminants that have molecular weights or other physical or chemical properties that differ from those of the target substance, wherein the purification is effected by sequential chromatographic and diafiltration separation steps in a cross-flow filtration system.

2. Description of the Related Art

Various methods of purification have been employed for the separation of substances from liquid samples. Precipitation, centrifugation, filtration, chromatography and evaporation have all been employed with varying success with respect to yield, time consumption, purity and cost.

In the area of biological purification, centrifugation, chromatography and filtration have been especially useful for obtaining highly valuables substances from liquid samples with yields ranging from 10 to 90 percent and purity as high as 95 percent.

In current applications of centrifugation, chromatography and filtration, it is generally understood that yield and purity are in an inverse relationship and that yields are significantly lower for each subsequent purification step. It is also well understood that these methods of centrifugation, chromatography and filtration are expensive, relatively slow, and employ equipment that is very difficult to clean prior to its reuse.

A particular problem in this respect is the cleaning of fixed bed chromatography columns, in which irregular flow channels tend to be formed through the chromatography resin. These irregular flow channels present a particular problem in the purification of biological substances, since a failure to completely clean the column can result in the contamination of subsequent batches.

An example is the purification of plasma proteins on ion exchange and affinity chromatography columns. If a batch of plasma tested to be free of virus is later learned to be contaminated with virus, it is nearly impossible to calculate the certainty of removal of the virus from the column. In addition, because biological liquids readily support the growth of bacteria, simple bacterial contamination and growth of organisms in chromatographic columns is by no means infrequent. Bacterial organisms and the endotoxins produced by the bacteria have contaminated countless batches of pharmaceutical products resulting in significant financial losses as well as adverse reactions in the recipients of the final product.

The frequently observed "rat tunnels" which present so many problems for validation of the cleaning process also negate a significant portion of the capacity and resolution capability of chromatography columns.

Another problem of fixed bed chromatography columns is compression of the resin, particularly in the case of softer gels such as agarose (e.g., Sepharose® gel, commercially available from Pharmacia). The joint problems of tunneling and compression significantly raise the cost of chromatography by necessitating large amounts of excess binding capacity. Another problem caused by compression and tunneling is loss of purity. High purity requires uniform elution of the target substance. Tunneling and compression prevent uniform distribution of the elution liquid, resulting in imprecise separation of the target substance from contaminants which have similar elution profiles to the target product as well as to randomly eluted contaminants entrapped in the compressed media.

In the case of monoclonal antibody purification, it is a common practice to pack a column with a ten-fold excess binding capacity. In a well-distributed system it would be possible to bind the entire target product with only a three-fold excess capacity, thereby reducing the cost of the chromatography media three-fold.

One common approach to decreasing tunneling and compression is to lower the operating pressure of the column by reducing the flow rate. Although the practice of reducing the flow rate decreases the compression of the resin, it significantly increases the processing time and in many cases adversely effects the resolution and the yield of the process.

Tangential flow filtration utilizes membranes of various pore sizes for separating substances in liquids by pumping the liquid parallel to the membrane surface. Although this process has proven effective in the concentration of substances suspended in water and/or buffers, it has not proven widely useful in the purification of compounds in solution. The first problem of this method is that the pore size is not sufficiently uniform to allow for the separation of two closely sized particles. In addition, substances in the liquid mixture, especially proteins and lipids, bind to the surface of the membrane, a phenomenon referred to as "gel layer polarization," changing the effective pore size as well as the surface chemistry of the membrane.

Fluidized bed chromatography is another means of separating substances from liquid mixtures. Fluidized bed chromatography is more commonly utilized in the chemical and petroleum industries. Fluidized bed columns are frequently 10 feet high or higher and 9 to 12 inches in diameter. Pharmaceutical and bioprocess columns are usually less than 3 feet high and have a wide variety of diameters in the general range of from 1 to 24 inches, depending on the compression characteristics of the resin. The advantages of a fluidized bed are higher flow rates at lower pressures as compared to fixed bed chromatography. Although the higher flow rates offer certain advantages to the chromatographic separation, the method has several shortcomings. The method requires larger diameter resins that are neutral to gravity or buoyant. These larger, 100 to 300 micron mean diameter resins have less surface area per unit volume than smaller, 1 to 100 micron resins used in fixed bed columns, and correspondingly have less surface binding capacity.

To minimize the loss of surface area and decrease density, the fluidized bed resins are highly porous structures. These resin particles, however, as a result of their porous character, are highly susceptible to cracking, thereby generating small particulates that block the inlet and outlet ports of the column.

The most significant problem of the fluidized bed is mixing. Since the column does not contain any static mixing means, the bed is conventionally mixed by means of air jets or by recycling the liquid to be separated through the column at a high flow rate. The high flow rate and limited mixing inhibit the uniform phase change required during elution of the product from the resin.

As a result of the above-described deficiencies in the art, there is a compelling need for a rapid, uniform, time- and cost-efficient system for purifying biological target substances from complex liquid sources. Such a system would desirably overcome the problems inherent in the various prior art separation technologies described above. Such a system also would desirably be readily scalable, being adaptable to process volumes of source material ranging from milliliters in the research laboratory to the thousands of liters commonly encountered in biopharmaceutical production. Finally, such a system would desirably be capable of use with source liquids of widely varying properties, including viscous complex solutions.

SUMMARY OF THE INVENTION

The present invention relates to a purification method that employs one or more cross-flow filter elements and one or more types of chromatography resins, in combination, to provide purification with advantageous yield, product purity, and cost- and time-efficiency.

The cross-flow filter module(s) used in the practice of the present invention may be of any suitable type, including for example cross flow filters such as hollow fiber filters, spiral filters, plate and frame filters, cassette filters, stir cells, tubular filters, ceramic filters, etc.

The method of the invention involves purifying target biological substance(s), such as for example selected proteins, antibodies, antigens, clotting factors, glycoproteins, and hormones, from source liquids containing contaminants that have molecular weights or other physical or chemical properties that differ from those of the target substance, wherein sequential chromatographic and diafiltration separation steps accomplished in a cross-flow filtration system.

The purification method of the invention provides high yields and rapid isolation of proteins, antibodies, growth hormones and other biologically significant substances from complex liquid sources, e.g., plasma, plasma fractions, milk, colostrum, cheese whey, cell culture and tissue culture fluids, and tissue and cell homogenates.

Further, the method of the invention may be applied to traditional purification methodologies to increase the yields of the traditional separations and to render those traditional methods suitably clean to allow for reuse and decontamination of affinity and/or filtration media as well as apparatus surfaces used in such purifications.

More specifically, the present invention in one aspect relates to a process for purifying a target substance from a source liquid, such process in one embodiment comprising the steps of:

1) contacting the source liquid with a chromatography resin;

2) incubating the source liquid with the chromatography resin for a sufficient contact time to allow the resin to bind a desired fraction of target substance;

3) recirculating the chromatography resin in a cross-flow filter system wherein the following steps are performed:

a) concentrating the chromatography resin and separating contaminants from the chromatography-resin-bound target substance by diafiltration;

b) eluting the target substance from the chromatography resin; and c) separating the target substance from the chromatography resin by diafiltration;

4) recovering the target substance; and 5) optionally concentrating the target substance.

The purification method may further comprise optional initial steps of (a) clarification of the source liquid to remove any undesirable particulates that are present and that have the potential to clog pores or orifices in later steps, and (b) concentration or dilution of the source liquid such that the step of contacting the source liquid with the chromatography resin may proceed most efficiently. These steps are preferably performed by cross-flow filtration, with addition of a selected amount of liquid to the system to yield a clarified source liquid of desired concentration for use in the subsequent incubation step.

The purification process of the present invention may further comprise added steps leading to isolation of additional target substance(s); in these added steps the permeate generated by the concentration and diafiltration of the chromatography resin, prior to elution, may be passed to a second chromatography resin or a series of chromatography resins and steps (1)–(4) are repeated. Alternatively, or additionally, the purification process of the present invention may further comprise repetition of steps (1)–(4) applied to diafiltrate from step 3(a) above, to increase the yield of target substance.

The purification method may advantageously employ a chromatography resin comprising rigid spherical cellulose beads with bound affinity ligands in the chromatographic separation step(s).

The method of the invention in another aspect comprises a method for purifying an immunoglobulin from a source liquid, comprising the steps of contacting the source liquid with a chromatography resin, wherein the chromatography resin comprises Protein A linked to rigid, non-porous spherical beads;

incubating the source liquid with the chromatography resin for a sufficient contact time to allow the resin to bind a desired fraction of the immunoglobulin;

recirculating the chromatography resin in a cross-flow filter system wherein the following steps are performed:

concentrating the chromatography resin and separating contaminants from the chromatography-resin-bound immunoglobulin by diafiltration;

eluting the immunoglobulin from the chromatography resin;

recovering the immunoglobulin from the chromatography resin by diafiltration; and optionally concentrating the immunoglobulin.

In a further aspect, the present invention comprises a purification apparatus, for separating and concentrating a target substance from a source liquid, such apparatus comprising:

a first reservoir constructed and arranged for holding a solid-phase chromatography resin material, and for selectively flowing liquid into and out of said first reservoir;

a solid-phase chromatography resin material disposed in said first reservoir;

a first cross-flow filtration module for separating liquids into permeate and retentate streams, provided with means for flowing liquid in and permeate and retentate liquid streams out of said first cross-flow filtration module;

a second reservoir constructed and arranged for capturing and holding the permeate liquid stream, and for selectively flowing liquid into and out of said second reservoir;

a second cross-flow filtration module for concentrating a liquid stream, provided with means for flowing liquid in and permeate and retentate liquid streams out of said second cross-flow filtration module;

a collection vessel constructed and adapted for capturing the concentrated liquid stream from the second cross-flow filtration module; and conduit, valve and pump means constructed and arranged for:

providing make-up liquids to the first and second reservoirs;

selectively flowing a source liquid to the first reservoir charged with a chromatography resin to form a slurry;

incubating the source liquid with the chromatography resin by recirculating the slurry from the first reservoir to the first cross-flow filtration module and returning both the permeate and retentate liquid streams to the first reservoir;

recirculating the slurry in a cross-flow filter in a flow pathway adapted for:
concentrating the slurry and separating contaminants from the slurry by diafiltration;
eluting the target substance from the chromatography resin; and
separating the target substance from the chromatography resin by diafiltration;

capturing the target substance in the second reservoir;

concentrating the target substance by flowing it from the second reservoir through the second cross-flow filtration module; and recovering the concentrated target substance from the flow pathway of the second cross-flow filtration module in the collection vessel.

In preferred embodiments of the apparatus, the first and second reservoirs are provided with thermal jackets to maintain appropriate process temperatures.

In another aspect, the invention relates to a method of purification of a liquid containing a target substance, comprising the steps of contacting the liquid with a chromatography resin to bind the target substance thereto, and cross-flow filtering the target substance-bound chromatography resin under elution conditions to recover a filtrate comprising the target substance.

Such method may be carried out to effect a separation selected from the group consisting of:

separating the liquid to produce a vaccine or vaccine component;

separating plasma or a plasma fraction into its constituent parts;

separating clostrum into its constituent parts;

separating milk into its constituent parts;

separating whey into its constituent parts;

separating a fermentation fluid into its constituent parts;

separating insect cell culture fluid into its constituent parts;

separating viral culture fluid into its constituent parts;

separating an immunoglobulin from an immunoglobulin-containing culture of bacteria, yeast, fungus, insect cells, or animal cells;

separating an immunoglobulin from serum;

separating an immunoglobulin from plasma or a plasma fraction;

separating an immunoglobulin from whole blood;

separating an immunoglobulin from milk;

separating an immunoglobulin from clostrum;

separating an immunoglobulin from whey;

separating an immunoglobulin from ascites fluid;

separating a clotting factor from whole blood;

separating a clotting factor from plasma;

separating a clotting factor from serum;

separating a clotting factor from a clotting factor-containing culture of bacteria, yeast, fungus, insect cells, or animal cells;

separating a clotting factor from milk;

separating a clotting factor from whey;

separating a clotting factor from clostrum;

separating a clotting factor from ascites fluid;

separating a protein from a protein-containing culture of bacteria, yeast, fungus, insect cells, or animal cells;

separating an antigen from an antigen-containing culture of bacteria, yeast, fungus, insect cells, or animal cells;

separating an antigen from a viral culture containing same;

separating a hormone from a hormone-containing culture of bacteria, yeast, fungus, insect cells, or animal cells;

separating a hormone from serum;

separating a hormone from plasma or a plasma fraction;

separating a hormone from whole blood;

separating a hormone from plasma;

separating a hormone from serum;

separating a hormone from milk;

separating a hormone from whey;

separating a hormone from clostrum;

separating a hormone from ascites fluid;

separating a hormone from tissue;

separating a glycoprotein from a viral culture;

separating a glycoprotein from a glycoprotein-containing culture of bacteria, yeast, fungus, insect cells, or animal cells;

separating a glycoprotein from serum;

separating a glycoprotein from plasma or a plasma fraction;

separating a glycoprotein from whole blood;

separating a glycoprotein from plasma;

separating a glycoprotein from serum;

separating a glycoprotein from milk;

separating a glycoprotein from whey;

separating a glycoprotein from clostrum;

separating a glycoprotein from ascites fluid; and separating a glycoprotein from tissue.

A further aspect of the invention relates to a method of separating a liquid in a separation system comprising a bioreactor, a chromatographic resin reservoir, a first cross-flow filtration module, a second cross-flow filtration module, and a third cross-flow filtration module, such method comprising clarifying the perfusate of the bioreactor in the first cross-flow filtration module to yield a permeate, flowing the permeate to the chromatographic resin reservoir and flowing chromatographic resin and permeate to the second cross-flow filtration module for concentration, diafiltration and elution to yield an eluate, and flowing the eluate to the third cross-flow filtration module for concentration and diafiltration therein.

The invention in another aspect relates to a method of purifying at least one target substance from a source liquid containing a bioactive contaminant, comprising the steps of:

contacting the source liquid with a chromatography resin;

incubating the source liquid with the chromatography resin for a sufficient contact time to bind to the chromatography resin at least one target substance from the source liquid;

recirculating the chromatography resin in a cross-flow filter wherein the following steps are performed:
concentrating the chromatography resin by diafiltration;
eluting the target substance from the chromatography resin; and separating the target substance from the chromatography resin by diafiltration;
recovering the target substance; and
optionally concentrating the target substance;
further comprising inactivating the bioactive contaminant during said method.

Another aspect of the invention relates to a process for purifying one or more target substances from a source liquid containing such target substances. The process comprises:
contacting the source liquid with a chromatography resin;
recirculating the chromatography resin in at least one cross-flow filter wherein the following steps are performed:
concentrating the target substance and chromatography resin in the source liquid by tangential flow filtration;
diafiltering the chromatography resin in a filter comprising a membrane effective to retain the resin and pass species that are not bound to the resin;
eluting the target substance from the chromatography resin by contact with an elution membrane effective to retain the resin and pass the target substance(s);
separating the target substance from the chromatography resin by diafiltration recovering the target substance(s); and
optionally concentrating the target substance(s).

In another aspect, the invention relates to a process for purifying one or more target substances from a source liquid containing said target substances together with one or more viral species, such process comprising:
contacting the source liquid with a viral inactivation agent for the one or more viral species;
concentrating the target substance(s) in the source liquid by tangential flow filtration in a tangential flow filter comprising a membrane effective to concentrate at least 90% by weight of the target substance(s) in such filtration;
contacting the source liquid with a chromatography resin;
incubating the source liquid with the chromatography resin for a sufficient contact time to bind a desired fraction of the target substance(s);
recirculating the chromatography resin in a cross-flow filter wherein the following steps are performed:
concentrating the chromatography resin and separating contaminants from the chromatography-resin-bound target substance by diafiltration in a filter comprising a membrane effective to retain the resin and pass species that are not bound to the resin;
eluting the target substance from the chromatography resin by contact with an elution membrane effective to retain the resin and pass the target substance(s);
separating the target substance from the chromatography resin by diafiltration;
recovering the target substance(s); and
optionally concentrating the target substance(s), e.g., by contact with a concentration membrane effective to yield a concentrate comprising at least 90% by weight target substance(s).

In another aspect, the present invention relates to a method of manufacturing universal plasma from blood containing serological Group A and/or Group B antibodies, comprising contacting the blood containing serological Group A and/or Group B antibodies with a chromatography resin comprising corresponding Group A and/or Group B antigen, and recovering an antibodies-depleted blood product as the universal plasma.

Numerous other aspects, features and illustrative embodiments of the invention will be more fully apparent from the ensuing disclosure and appended claims.

DETAILED DESCRIPTION OF THE INVENTION, AND PREFERRED EMBODIMENTS THEREOF

Definitions, Materials and Equipment

Figure 1:
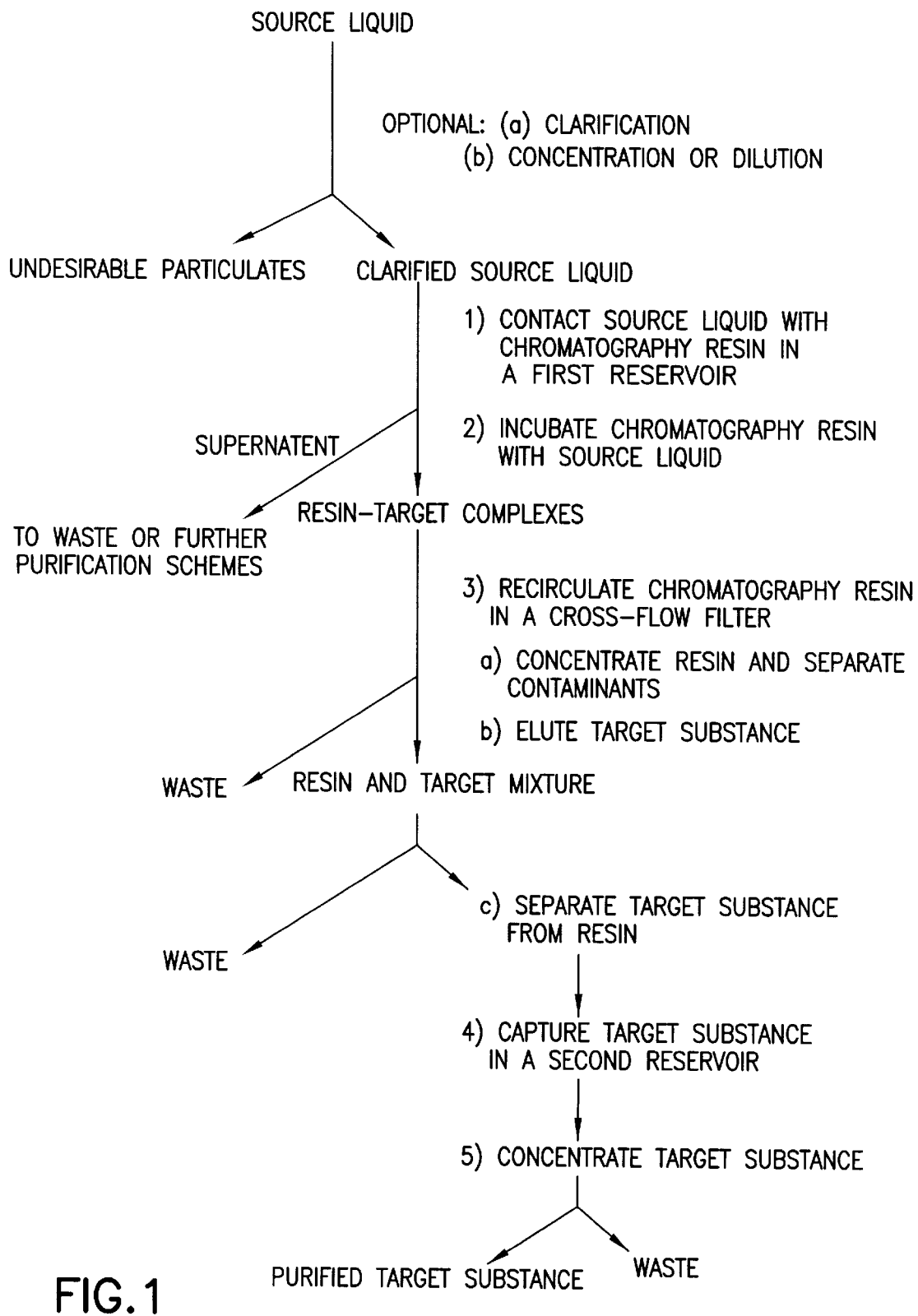
FIG. 1 shows a general scheme of a purification method according to one embodiment of the invention, using a cross-flow filtration based apparatus.

In the description of the present invention, certain terms are used as defined below.

A "source liquid" as used herein refers to a liquid containing at least one and possibly two or more biological substances or products of value which are sought to be purified from other substances also present. In the practice of the invention, source liquids may for example be aqueous solutions, organic solvent systems, or aqueous/organic solvent mixtures or solutions. The source liquids are often complex mixtures or solutions containing many biological molecules such as proteins, antibodies, hormones, and viruses as well as small molecules such as salts, sugars, lipids, etc. While a typical source liquid of biological origin may begin as an aqueous solution or suspension, it may also contain organic solvents used in earlier separation steps such as solvent precipitations, extractions, and the like. Examples of source liquids that may contain valuable biological substances amenable to the purification method of the invention include, but are not limited to, a culture supernatant from a bioreactor, a homogenized cell suspension, plasma, plasma fractions, milk, colostrum and cheese whey.

The term "target substance" refers herein to the one or more desired product or products to be purified from the source liquid. Target substances are typically biological products of value, for example, immunoglobulins, clotting factors, vaccines, antigens, antibodies, selected proteins or glycoproteins, peptides, enzymes, etc. The target substance may be present in the source liquid as a suspension or in solution. For convenience, the term "target substance" is used herein in the singular, but it should be understood that it may refer to more than one substance that is to be purified, either together as co-products or separately (e.g., sequentially) as discrete recovered components. "Contaminants" refers to materials in the source liquid that are different from the target substance(s) and are desirably excluded from the final target substance product(s). Typical contaminants include nucleic acids, proteins, peptides, endotoxins, viruses, etc. Contaminants that can be removed by the practice of the inventive method have one or more properties that differ from those of the desired product, e.g., molecular weight, charge, specific affinity for various ligands, and so forth. Many contaminants are bioactive, and their removal is imperative for the purified product to be usable in its end application. Additionally, because of deleterious effects that they may exert on the target products in subsequent usages, certain contaminants must be cleaned from the purification apparatus to extremely low and preferably undetectable levels. The method of the present invention enables highly efficient decontamination, as will be described in more detail hereinafter. "Cross-flow filter" refers herein to a type of filter module or filter cassette that comprises a porous filter element across a surface of which the liquid medium to be filtered is flowed in a tangential flow fashion, for permeation through the filter element of selected component(s) of the liquid medium. In a cross-flow filter, the shear force exerted on the filter element (separation membrane surface) by the flow of the liquid medium serves to oppose accumulation of solids on the surface of the filter element. Cross-flow filters include microfiltration, ultrafiltration, nanofiltration and reverse osmosis filter systems. The cross-flow filter may comprise a multiplicity of filter sheets (filtration membranes) in an operative stacked arrangement, e.g., wherein filter sheets alternate with permeate and retentate sheets, and as a liquid to be filtered flows across the filter sheets, impertpeate species, e.g. solids or high-molecular-weight species of diameter larger than the filter sheet's pore size, are retained and enter the retentate flow, and the liquid along with any permeate species diffuse through the filter sheet and enter the permeate flow. In the practice of the present invention, cross-flow filtration is a preferred separation method. Cross-flow filter modules and cross-flow filter cassettes useful for such filtration are commercially available from North Carolina SRT, Inc. (Cary, N.C.). Suitable cross-flow filter modules and cassettes of such types are variously described in the following United States patents of the inventor of the present invention: U.S. Pat. No. 4,867,876, "Filter Plate, Filter Plate Element, and Filter Comprising Same, issued Sep. 19, 1989; U.S. Pat. No. 4,882,050, same title, issued Nov. 21, 1989; U.S. Pat. No. 5,034,124, same title, issued Sep. 11, 1990; U.S. Pat. No. 5,034,124, same title, issued Jul. 23, 1991; U.S. Pat. No. 5,049,268, same title, issued Sep. 17, 1991; U.S. Pat. No. 5,232,589, "Filter Element and Support, issued Aug. 3, 1993; U.S. Pat. No. 5,342,517, "Filter Cassette Article," issued Aug. 30, 1994; U.S. Pat. No. 5,593,580, same title, issued Jan. 14, 1997; and U.S. Pat. No. 5,868,930, same title, issued Feb. 9, 1999; the disclosures of all of which are hereby incorporated herein by reference in their respective entireties. "Chromatography resin" refers herein to a solid phase that selectively or preferentially binds one or more components of the source liquid. In the practice of the invention, such "chromatography resins" can be selected from any of the group s of resins commonly described as affinity, ion exchange and ion capture resins. The resins need only possess a chemistry or an associated ligand that will selectively or preferentially capture a substance of interest from the source liquid. Useful chromatography resins typically comprise a support and one or more ligand(s) bound thereto that provide(s) the selective or preferential binding capability for the target substance(s) of interest. Useful supports include, by way of illustrative example, polysaccharides such as agarose and cellulose, organic polymers such as polyacrylamide, methylmethacrylate, and polystyrene-divinylbenzene copolymers such as for example Amberlite® resin, commercially available from Rohm & Haas Chemical Co., Philadelphia, Pa. It should be recognized that although the term "resin" is commonly used in the art of chromatography, it is not intended herein to imply that only organic substrates are suitable for resin substrate use, since inorganic support materials such as silica and glasses have utility as well. In the practice of the present invention, the resin may be in the form of beads which are generally spherical, or alternatively the resin may be usefully provide in particulate or divided forms having other regular shapes or irregular shapes. The resin may be of porous or nonporous character, and the resin may be compressible or incompressible. Preferred resins will be physically and chemically resilient to the conditions employed in the purification process including pumping and cross-flow filtration, and temperatures, pH, and other aspects of the liquids employed. The resin as employed in the practice of the present invention is preferably of regular generally spherical shape, nonporous and imcompressible.

"Affinity ligand" refers to a moiety that binds selectively or preferentially to a component of the source liquid through a specific interaction with a binding site of the component. In the practice of the invention, the affinity ligand is typically immobilized to a solid phase such as a resin. Examples of affinity ligands that can be bound to the resin support to provide chromatography resins useful in the process of the present invention include: protein A and protein A analogs, which selectively bind to immunoglobulins; dyes; antigens, useful for purification of associated antibodies; antibodies, for purification of antigens; substrates or substrate analogs, for purification of enzymes; and the like. Affinity ligands and methods of binding them to solid support materials are well known in the purification art. See, e.g., the reference texts *Affinity Separations: A Practical Approach* (Practical Approach Series), Paul Matejtschuk (Editor), Irl Pr: 1997; and *Affinity Chromatography,* Herbert Schott, Marcel Dekker, New York: 1997.

"Affinity chromatography resin" or "affinity resin" refers to a chromatography resin that comprises a solid support or substrate with affinity ligands bound to its surfaces. Illustrative, non-limiting examples of suitable affinity chromatography resins include spherical beads with affinity ligands bound to the bead surfaces, wherein the beads are formed of cellulose, poly-styrene-divinylbenzene copolymer, polymethylmethacrylate, or other suitable material. In the practice of the present invention, rigid beads that can withstand pumping and recirculation through a cross-flow filtration module while maintaining structural integrity (e.g., without significant breakage generating pore-clogging particulates) are preferred. Particularly preferred are rigid, non-porous cellulose beads with bound affinity ligands. An illustrative particularly preferred embodiment employs "Orbicell®" beads (commercially available from Accurate Polymers, Inc., Highland Park, Ill.) that can be covalently coupled, e.g., by well-known methods within the skill of the art, to suitable affinity ligands, e.g. Protein A.

"Ion exchange chromatography resin" or "ion exchange resin" refers to a solid support to which are covalently bound ligands that bear a positive or negative charge, and which thus has free counterions available for exchange with ions in a solution with which the ion exchange resin is contacted.

"Cation exchange resins" refers to an ion exchange resin with covalently bound negatively charged ligands, and which thus has free cations for exchange with cations in a solution with which the resin is contacted. A wide variety of cation exchange resins, for example, those wherein the covalently bound groups are carboxylate or sulfonate, are known in the art. Commercially available cation exchange resins include CMC-cellulose, SP-Sephadex®, and Fast S-Sepharose® (the latter two being commercially available from Pharmacia).

"Anion exchange resins" refers to an ion exchange resin with covalently bound positively charged groups, such as quaternary amino groups. Commercially available anion exchange resins include DEAE cellulose, QAE Sephadex®, and Fast Q Sepharose® (the latter two being commercially available from Pharmacia).

"Dialysis liquid" or "dialysis buffer" or "diafiltrate" all refer herein to the liquid used in the diafiltration step to carry away contaminants from the target substance-chromagraphy resin complexes. Suitable dialysis liquids aid in the removal of contaminants from the resin by acting to disrupt non-specific binding of contaminants to the chromatography resin without causing significant dissociation of the bound target substance from the resin. The dialysis liquid can be as simple as water or as complex as multicomponent solvent mixtures such as for example a solvent mixture containing 80% hexane, 15% acetonitrile and 5% isopropanol, wherein all percentages are by volume, based on the total volume of the mixture. More than one dialysis liquid may be employed sequentially, e.g., with the successive dialysis liquids having varying properties such as pH values, conductivity, solvent concentration, etc., designed to dissociate and remove varying types of contaminants that are non-specifically associated with the chromatography resin. An example of a dialysis liquid useful in the purification of selected proteins such as immunoglobulins is an aqueous buffered 0.4 M NaCl solution.

"Wash liquid" or "wash buffer" as used herein are synonymous with dialysis liquid or dialysis buffer, that is, liquids used to wash contaminants away from the chromatography resin to which is bound the target substance.

"Elution liquid" or "elution buffer" refers herein to the liquid that is used to dissociate the target substance away from the chromatography resin after it has been cleansed of contaminants. The elution liquid acts to dissociate the target substance without denaturing it irreversibly. Typical elution liquids are well known in the chromatography art and may have higher concentrations of salts, free affinity ligands or analogs, or other substances that promote dissociation of the target substance from the chromatography resin. "Elution conditions" refers to process conditions imposed on the target substance-bound chromatography resin that dissociate the (undenatured) target substance from the chromatography resin, such as the contacting of the target substance-bound chromatography resin with an elution liquid or elution buffer to produce such dissociation.

"Cleaning liquid" or "cleaning buffer" refers herein to the liquid that is used to wash the chromatography resin after the completion of the purification process. The cleaning liquid may contain a detergent, a virus-inactivating agent, or relatively high concentrations of salts, and may have a higher or lower pH than the liquids used during the purification process. Its purpose is to fully decontaminate the chromatography resin to render it ready for reuse. Typical cleaning liquids are well-known in the chromatography art.

"Storage liquid" or "storage buffer" refers herein to the liquid in which the chromatography resin is suspended between uses. Storage liquids, in addition to buffering ions, may also contain microbicides or other preservatives. Such storage liquids are well known in the chromatography art.

Purification Process

FIG. 1 shows a general scheme that may be used to purify a target substance in the practice of the invention, as described in more detail below. Initially, the source liquid is optionally (a) clarified to remove potentially interfering particulates and (b) concentrated or diluted, as necessary for the subsequent purification steps. If the source liquid is sufficiently free of particulates and/or of an appropriate concentration in its originally supplied form, either or both of these steps (a) and (b) may be omitted.

The source liquid is then (1) transferred to a first reservoir where it is contacted with a chromatography resin, which selectively or preferentially binds the target substance. The source liquid is (2) incubated with the chromatography resin for a sufficient contact time to lead to binding of a desirably high percentage of the target substance to the chromatography resin, and to form resulting resin-target complexes. During the incubation the source liquid is stirred by an appropriate means, including cross-flow filtration where the permeate is recycled back to the reservoir, so that contact between the resin and the target substance is fully assured.

The resin is (3) recirculated through a cross-flow filter where (a) the resin is concentrated; (b) the resin is diafiltered against a first diafiltrate liquid which is selected to dissociate non-specifically binding components from the resin while not disrupting the resin-target complexes; (c) the substance of interest is eluted from the resin by treatment with a second diafiltration liquid which is selected to dissociate the specific target-resin complexes; (d) the target is diafiltered away from the resin. The diafiltrate containing the target substance is (4) captured in a second reservoir; and (5) the target substance is concentrated to a useful concentration.

The optional first clarification step is performed to remove from the source liquid particulate contaminants whose mean diameters are larger than the pore size of the separating cross-flow filter module used in the subsequent steps. This first clarification step, where required, avoids the concentration of particulate material in the chromatography resin slurry, and it additionally prevents the particulate contaminants from dissolving during the later steps of the purification process and contaminating the purified target substance.

The clarification step can be accomplished by methods well-known in the purification art, for example, centrifugation, gravity separation, precipitation, flocculation-assisted sedimentation, decanting, normal filtration, sieving, absorption, adsorption and tangential flow filtration. Alternatively, the source liquid may already be sufficiently clean to make this step unnecessary.

Figure 2:
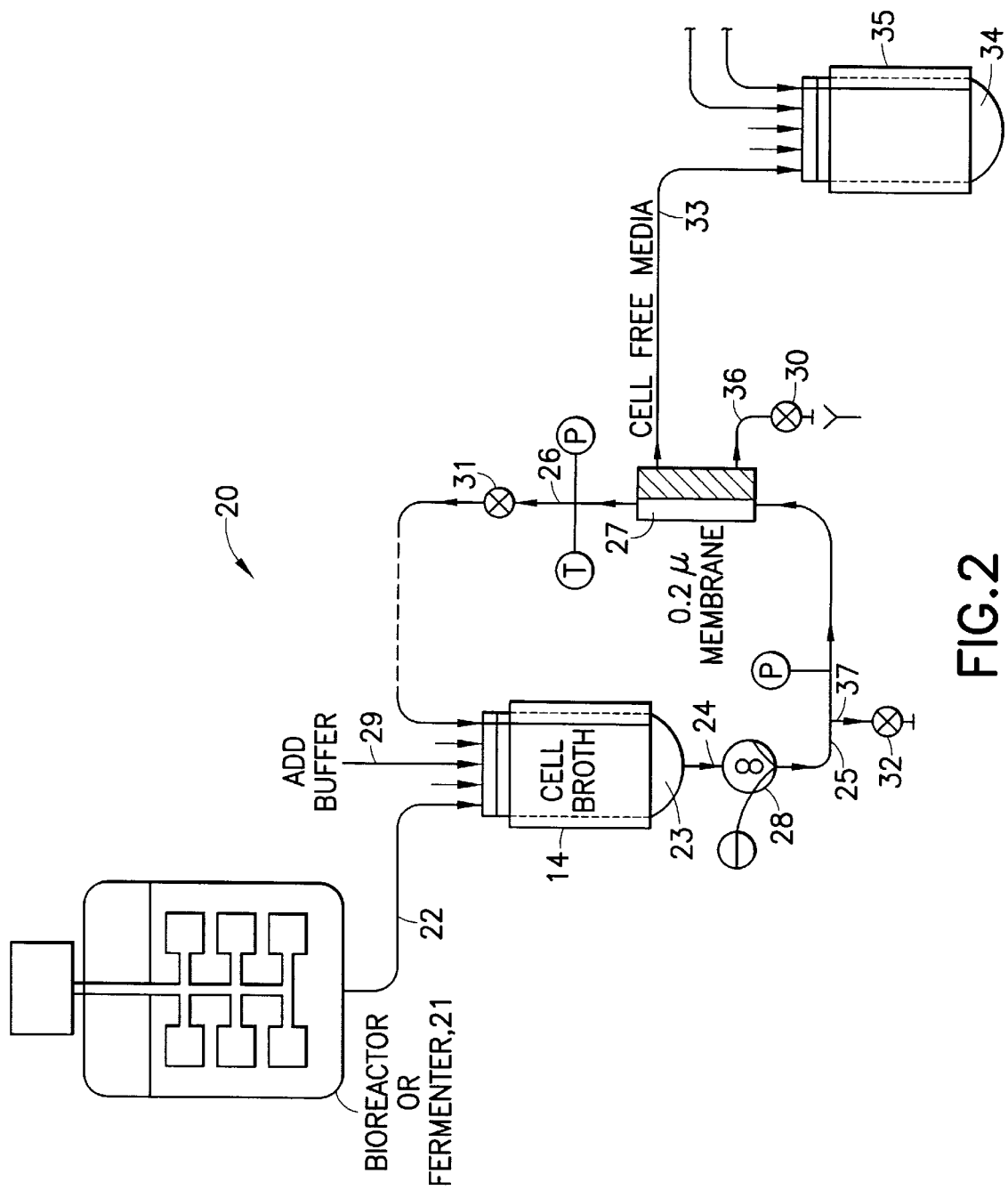
FIG. 2 shows a schematic representation of an apparatus useful for clarifying a source liquid to be submitted to subsequent purification steps.

FIG. 2 shows a schematic flowsheet of a system 20 for clarification of a source liquid by cross-flow filtration and transfer of the clarified source liquid to a reservoir for subsequent purification steps. Referring to FIG. 2, the source liquid, typically a supernatant or a suspension originating in a fermentor or bioreactor 21, is carried via conduit 22 to reservoir 23, which is provided with a thermal jacket 24 to keep the source liquid at a suitable temperature. Pump 28 is activated and the source liquid is circulated from reservoir 23 through cross-flow filter module 27 via conduits 24, 25, and 26, with valves 30 and 32 in the closed position, and valve 31 optionally open to return the retentate to the reservoir 24 for additional filtration cycles. Make-up buffer is added to reservoir 23 via conduit 29. Permeate (clarified source liquid) is carried via conduit 33 to a second reservoir 34 where it is held for subsequent purification steps. Reservoir 34 is also provided with a thermal jacket 35 to keep the clarified source liquid at an appropriate temperature. After use, when the system is to be purged and cleaned, valves 30 and 32 are opened and conduits 36 and 37 carry wash liquid to suitable drain and/or collection means.

The source liquid is then contacted with an appropriate chromatography resin, in reservoir 34 as depicted in FIG. 2. It is possible to add the chromatography resin to the reservoir already containing the (optionally clarified) source liquid, or alternatively the chromatography resin may be charged to the reservoir and the source liquid thereafter added, or the contacting of the chromatography resin and the source liquid may be carried out in any other suitable manner, e.g., in a batch, semi-batch or continuous manner.

Suitable chromatography resins for use in this step may be in the form of beads or other particulate or finely divided forms capable of binding the target substance. The beads are preferably sized with a diameter that is about 1.5 to 10 times larger than the pore size of the separating filter. The chromatography resin can be selected from any of the groups of resins commonly described as affinity, ion exchange and ion capture resins, and a wide variety of resins of such types is readily commercially available. The resins possess a chemistry or ligand chemistry that will capture the substance of interest and bind the target substance to the resin.

A particularly useful chromatography resin is provided in the form of uniformly spherical, non-porous, rigid, non-agglomerating, particles that are in the range of about 0.1 to 1,000 microns in size and have a low affinity for nonspecific binding. In one particularly preferred embodiment of the invention, the chromatography resin comprises cellulose beads, 1 to 3 microns in diameter, with Protein A ligands covalently bound to its surface. Such beads are highly useful in the purification of monoclonal antibodies from tissue culture and mouse ascites fluid. Beads of such type are commercially available under the trademark "Orbicell®" from Accurate Polymers, Inc. (Highland Park, Ill.).

Figure 3:
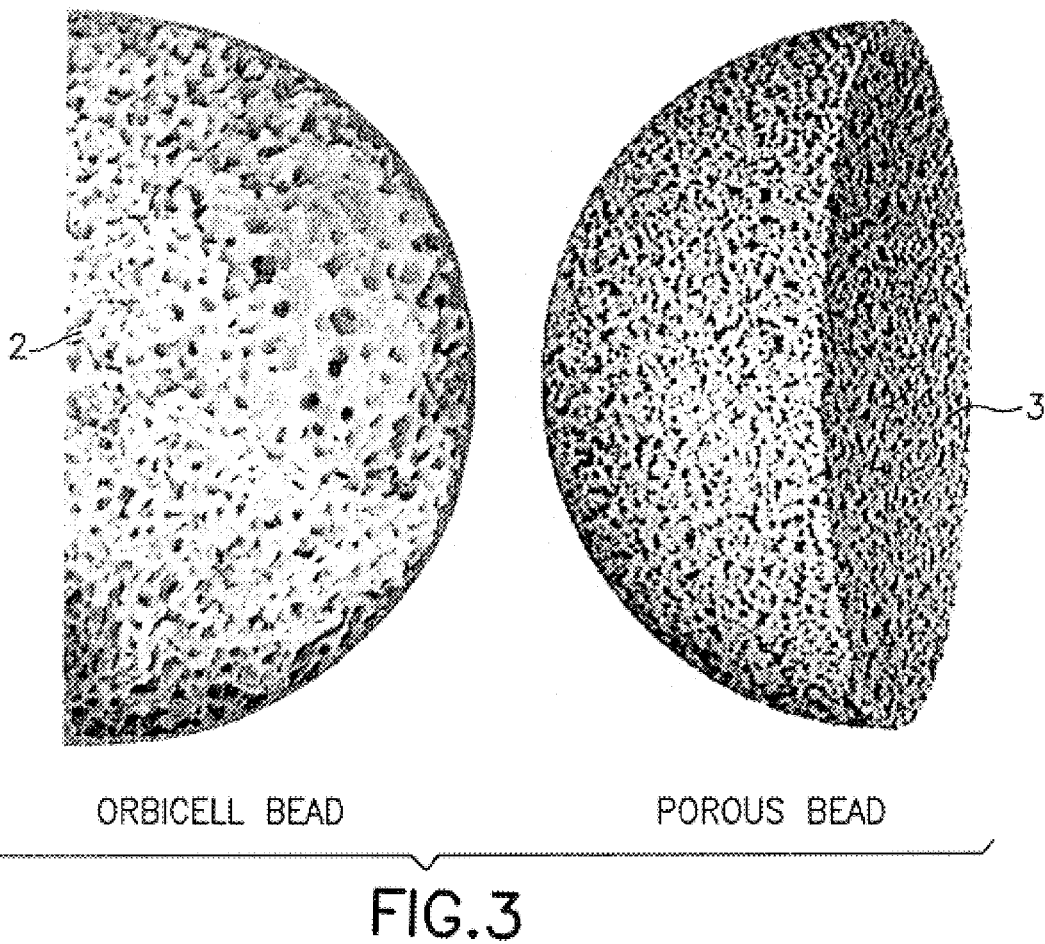
FIG. 3 shows the microscopic topography of an Orbicell® bead used in a chromatography resin, in comparison with that of a standard prior art porous bead.

FIG. 3 depicts the surface and cross-section of such Orbicell® beads 2, showing their high surface area but lack of interior porosity, as a result of which such beads possess high mechanical strength, as contrasted to standard porous beads 3. The high strength and rigidity of the Orbicell® beads make them especially suitable for recirculation through the cross-flow filters, since they are not prone to breaking into smaller particulates which can clog filter pores and they are not prone to compressing and forming irregular flow pathways. Other types of beads of corresponding character to such Orbicell® beads are commercially available and usefully employed in the practice of the present invention.

Figure 4:
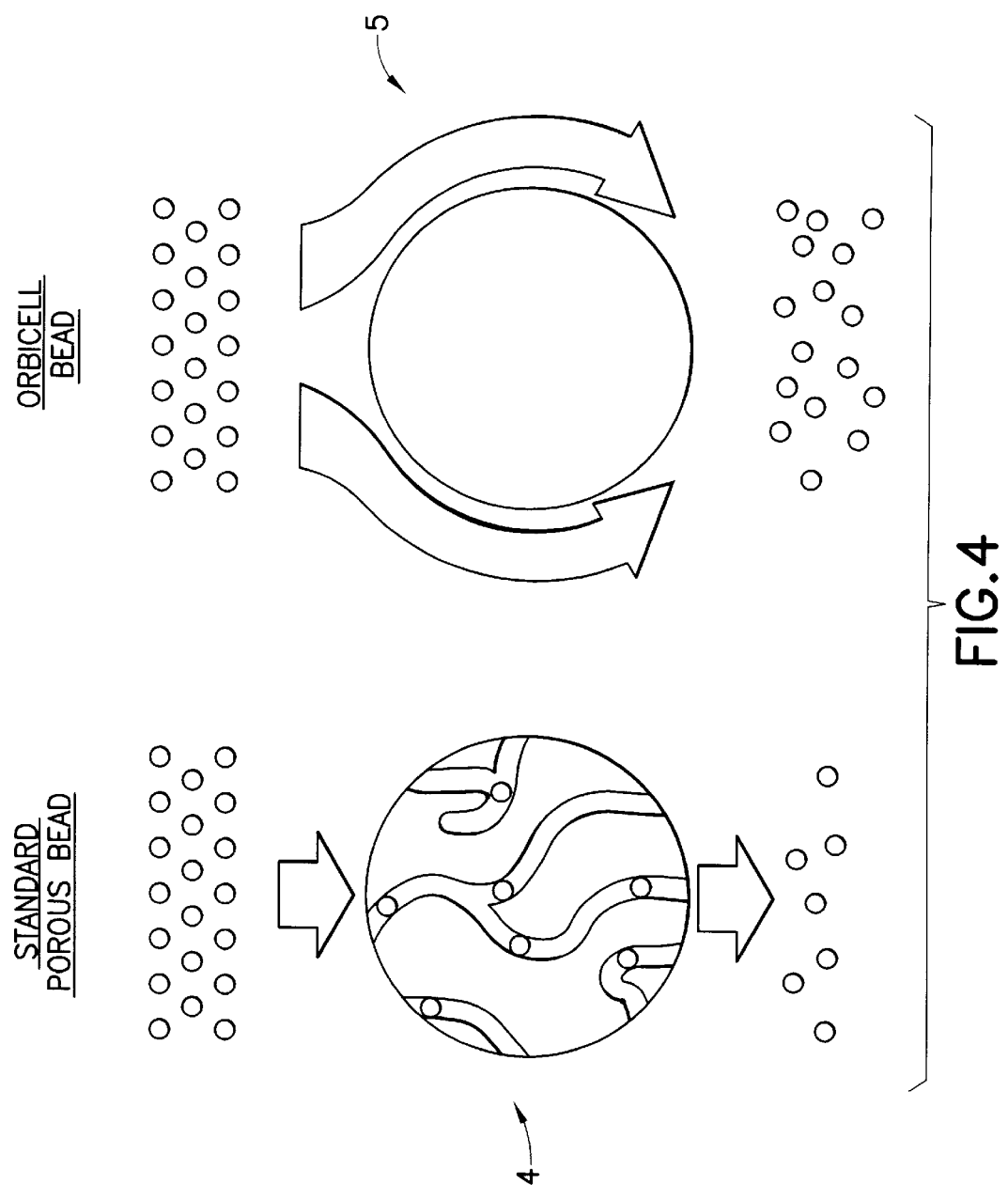
FIG. 4 shows a schematic illustration of the flow pathways around an Orbicell® bead, by comparison with the flow pathways around and through a standard prior art porous bead.

FIG. 4 schematically illustrates the simpler flow pathways present when using the Orbicell® beads 4 as opposed to porous beads 5 of the type used in prior art bioseparations. Such prior art porous beads are less advantageous in their physical properties with respect to their resilience and resistance to breakage under extended pumping and recirculation conditions, than the non-porous beads preferably used in the practice of the present invention. An additional benefit of non-porous beads is that contaminants would not be entrapped in the pore only to elute out during the elution step lowering the purity of the target substance.

Figure 5:
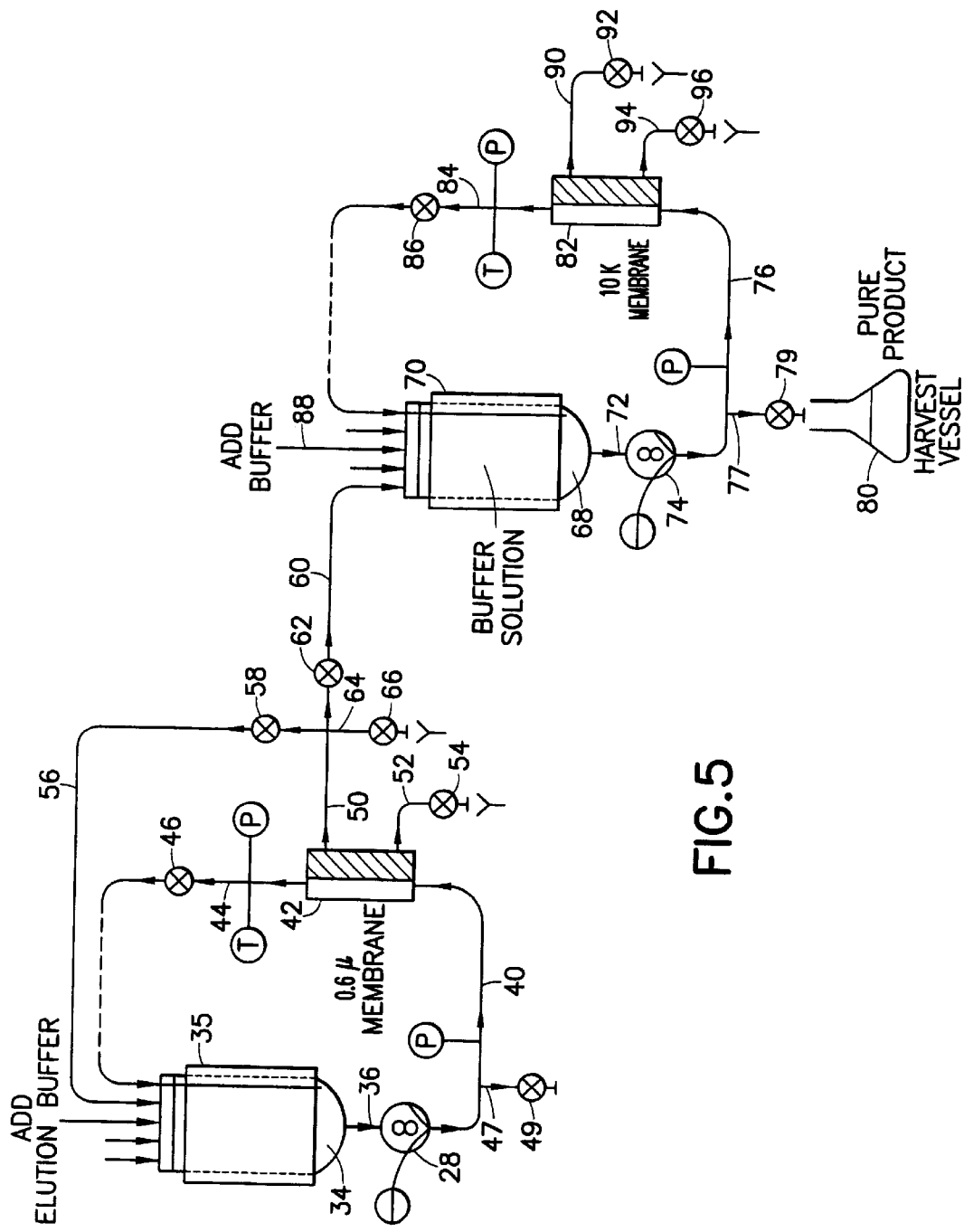
FIG. 5 shows a schematic representation of an apparatus useful for carrying out the cross-flow chromatographic purification, elution, recovery and concentration steps of the method of the present invention, in one embodiment thereof, in which cross-flow filter module is employed.

Referring now to FIG. 5, the chromatography resin-source liquid slurry is incubated for an appropriate contact time in reservoir 34 following the initial processing described hereinabove with reference to FIG. 2. A simple method of incubation may entail stirring or shaking the reservoir 34 containing the slurry. In a preferred embodiment of the invention, the resin/liquid slurry is recirculated through line 36 under the action of pump 38 and through line 40 (having drain line 47 containing valve 49 connected thereto) across the separating cross-flow filter module 42, with the liquid being recycled from the filter module 42 through line 44 having backpressure valve 46 to the reservoir 34 at a volumetric flow rate sufficient to keep filter 42 clean. Permeate is returned to reservoir 34 through line 50 through open valve 58 through line 56 providing an appropriate contact or incubation time for the liquid in the reservoir.

The preferred contact (incubation) time in the reservoir 34 depends on the particular chromatography resin employed and its concentration of binding sites for the target substance, as well as the relative concentration of beads and target substance. The reaction time of the chemistry will vary from ligand to ligand, but the higher the concentration of available binding sites compared to the target substance, the shorter the preferred incubation time. It is contemplated that excess resin may be optimized in various applications at 1.2 to 10 fold higher concentration than the target substance. A further consideration in the optimization of the method is the concentration of the resin suspended in the liquid. Resin concentrations in the range of from 1 to 64 percent (by weight, based on the total weight of the combined resin and liquid material) may be advantageously utilized, with from about 10 to about 50 percent resin concentrations (on the same basis) being considered optimum.

Temperature is controlled during the incubation step by the thermal jacket 35 (or other heat transfer means, such as for example a heating coil disposed in the liquid volume in the reservoir 34, a recirculation heater external of the reservoir, through which liquid is flowed from the reservoir, heated to suitable temperature in the heater unit, and returned to the liquid volume of the reservoir), to provide the liquid and resin mixture with a suitable temperature to preserve the target substance's activity. Suitable temperatures for such purpose may be readily determined within the skill of the art and without undue experimentation.

The transfer of the source liquid into the reservoir for contact with the chromatography resin (step (1) above) and the incubation of the source liquid with the chromatography resin (step (2) above) can be accomplished concurrently by simultaneously adding the source liquid to the chromatography resin reservoir while removing an equal volume of resin-free liquid. The controlling element in this embodiment of the invention is that the residence time of the source liquid in the reservoir must be long enough to allow for essentially complete binding of the target substance to the chromatography resin. This objective is readily accomplished through the separating cross-flow filter module 42. The permeate flow equal to the infused source liquid volume is removed from the loop in line 64 having valve 66 therein. The excess permeate is sent back to the resin reservoir in line 56 containing valve 58 therein.

The contaminants and excess liquid are separated and dialyzed away from the chromatography resin, now bound to the target substance, by means of the separating cross-flow filter module 42. The resin slurry is recirculated across the cross-flow filter module for separation therein and retentate liquid is returned to the reservoir. The permeate liquid is directed to one or more of: (1) a drain (by line 52 containing valve 54 therein); (2) a second reservoir, not shown, containing a subsequent resin (by line 64 containing valve 66); (3) an independent processing step. The resin may be concentrated to concentrations ranging from about 0.1 to about 64 percent by volume. In one preferred embodiment of the invention, the resin is concentrated to about 50% resin by volume.

The volume of wash buffer required to wash the chromatography resin depends on the concentration of resin in suspension. For example, if the resin slurry is 100 liters of a 1% resin solution, then the volume required to wash the resin ten-fold is 1,000 liters. If the resin slurry is 10 liters of a 10% percent resin solution, then the volume required is 100 liters.

The time required to wash the chromatography resin also depends on the concentration of resin in suspension, because of the effect of resin concentration on flow rate in the cross-flow filter module. For example, if the resin slurry is 10 liters of a 25% resin solution, then the permeate rate might be 100 L/$m^2$-h. If the resin slurry is 5 liters of a 40% resin solution, then the permeate rate might be only 10 L/$m^2$-h. Therefore the time required to wash the chromatography resin slurry ten-fold with wash buffer using a 1.0 $m^2$ cross-flow filter module would be one hour for a 20% suspension, and a 40% suspension would require a wash time of five hours.

After the resin is concentrated, diafiltration is begun by addition of an appropriate dialysis liquid to the reservoir 34. Suitable dialysis liquids (or "diafiltrate" or "dialysis buffer") aid in the removal of contaminants from the resin by acting to disrupt non-specific binding of contaminants to the chromatography resin without causing significant dissociation of the bound target substance from the resin. The dialysis liquid can be as simple as water or as complex as multiple solvent mixtures such as 80% hexane, 15% acetonitrile and 5% isopropanol solutions.

The number of dialysis buffer exchanges during this diafiltration step preferably ranges from 3 to 25. The preferred number of dialysis buffer exchanges is determined based upon the retention characteristics of the contaminants with respect to the separating cross-flow filter module 42 and the desired purity of the target product. Dialysis buffer exchange (diafiltration) to remove final traces of contaminants from the resin slurry is accomplished by adding makeup dialysis buffer to the slurry reservoir at the same flow rate as the permeate rate. This procedure can easily be automated using level controls, load cells, or flow meters. The extent of buffer exchange is measured in Volume Replacements, defined as the ratio of the cumulative volume of buffer added to the resin slurry reservoir, divided by the starting volume of the resin slurry. The extent of exchange or dilution of the original supernatant with the added buffer is a geometric function. Set out below is a table of supernatent dilution and Volume Replacements, for an illustrative embodiment of the invention.

| Supernatant Dilution vs. Volume Replacements | |
|---|---|
| Volume Replacement | Concentration of Replacement Buffer in Retentate |
| 0 | 0 |
| 1 | 50% |
| 2 | 75% |
| 3 | 87.5% |
| 5 | 96.9% |
| 7 | 98.7% |
| 10 | 99.8% |

The optimal separating cross-flow filter module 42 preferably has a membrane pore size that is 1.5 to 10 times smaller than the mean diameter of the chromatography resin beads. The channel height of the separating cross-flow filter module is desirably 1.2 to 10 times larger than the mean diameter of the chromatography resin beads to provide satisfactory clearance and efficient hydrodynamic behavior of the filter module. A highly preferred design of the separating cross-flow filter module is an open channel module with even distribution of flow to the retenate channels. In one preferred embodiment of the invention, the chromatography resin beads have a mean diameter of approximately 1 to 3 microns, the cross-flow filter has a filter element wit a mean pore size of about 0.6 microns, and the height of the retentate channel is 0.5 mm. A cross-flow filter module suitable for this purpose is commercially available from North Carolina SRT Inc. (Cary, N.C.).

In one embodiment of the inventive method, the permeate from the diafiltration step is passed through line 50 (containing drain line 64 with valve 66 therein), valve 62 and line 60 to an additional reservoir 68 containing a second resin which effects a second separation of substances from the starting material.

For example, immunoglobulins to specific antigens are purified sequentially from plasma by the use of a series of affinity chromatography resins, each linked with specific viral antigens.

In another illustrative example, milk proteins are separated sequentially from whey by use of a series of specific chromatography resins, each linked with ligands that bind targeted proteins. These ligands can be ion exchangers, immunoglobulins, native proteins, or any affinity ligands that bind selectively or preferentially to the targeted proteins and can be linked to the resins. In yet another illustrative example, plasma proteins are sequentially purified from whole plasma or from plasma fractions by use of resins linked with antibodies to the targeted proteins.

After diafiltration to remove contaminants, the target substance is eluted and recovered from the chromatography resin. The specific chemistry used for elution depends on the nature and strength of the chromatography resin-target substance interaction. The elution and recovery procedure is similar to the diafiltration step described above. An appropriate elution liquid which dissociates the target substance from the chromatography resin is added to the resin slurry reservoir (e.g., to reservoir 34 in line 48) at a rate equal to the permeate rate until the desired yield is obtained. This procedure will be extremely useful when the chromatography resin is an ion exchange resin, because the increase in ion concentration can be readily monitored using a conductivity meter, and the ion concentration will increase at a specific rate over time. In the case where the chromatography resin is an affinity resin, it is useful to first add a concentrated form of the elution buffer to the resin slurry reservoir to enhance the changeover from diafiltration buffer to elution buffer.

For example, in the elution of monoclonal antibodies from a Protein A resin, the resin slurry pH is lowered to a suitable value, e.g., on the order of pH 2.5, by addition of a measured volume of 1.0 M glycine buffer. The resin slurry is then diafiltered against ten volumes of 0.1 M glycine buffer.

A modification of the elution step involves using a different pore size cross-flow filter module. For example, when eluting a plasma protein from the chromatography resin it would be useful to change the cross-flow membrane to a membrane which would retain any contaminating virus or protein-virus complexes which were not removed during the earlier diafiltration step 3(a).

For such modification (see FIG. 6) the first cross-flow filter is 83 and the second filter would be 42. The resin slurry is first concentrated and diafiltered through cross-flow filter 83 by pump 38 through line 40 with valve 57 closed and valve 81 open. From filter 83 the diafiltered slurry is flowed through open valve 91 and line 89 past closed valve 46 back to reservoir 34. The permeate of this step can flow to drain or a subsequent purification through line 93 and open valve 99. For the elution step valves 81 and 91 are closed and valves 57 and 46 are opened so that the eluted permeate can flow through the tighter filter 42 to reservoir 68 through open valve 62 and line 60. The filter module 83 is joined to line 93 containing valve 99 therein, as well as to line 85 containing valve 87 therein, to accommodate flow of permeate out of the filter module, or the passage of another mass transfer fluid (in cocurrent or countercurrent flow on the opposite side of the filter element from the liquid being filtered) to maximize mass transfer gradient and flow of particular species into or out of the retentate liquid.

Figure 6:
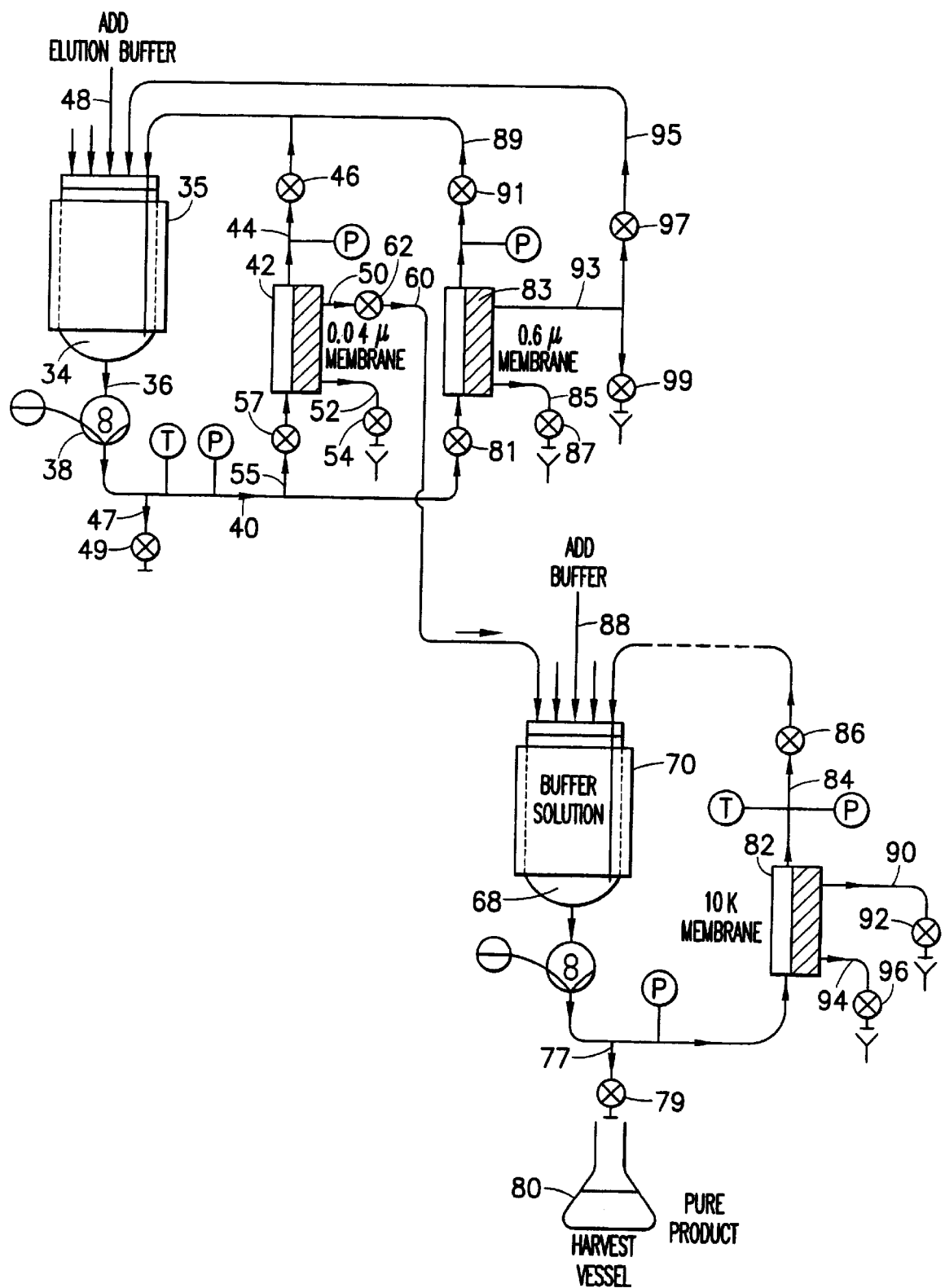
FIG. 6 shows a schematic representation of an alternative apparatus useful for carrying out the cross-flow chromatographic purification, elution, recovery and concentration steps of the method of the present invention, in another embodiment thereof, employing additionally a second cross-flow filter module of different porosity than the first.

The diafiltration and elution operations may all be carried out in the first reservoir 34 as shown in FIG. 6 and the resulting permeate comprising the target substance may then be passed to the second reservoir 68 for final treatment, e.g., buffering thereof or other treatment, with additional filtration in the cross-flow filter 82 and final harvesting into the harvest vessel 80. In such arrangement, some of the permeate from the first cross-flow filter module 83 in line 93 can be recycled through another cross-flow filter such as a nanofilter to minimize the amount of buffer utilized.

It will therefore be appreciated that a number of alternative apparatus arrangements may be constructed, arranged and operated, to carry out the separation method of the present invention in various embodiments thereof.

In another illustrative embodiment of the invention, a milk protein is eluted from an ion exchange resin to yield a protein product of enhanced purity by using a different pore size separating cross-flow module to effect a size separation due to the fact that ion exchange does not have the specificity of more expensive affinity resins.

FIG. 6 as illustrated depicts a purification system that employs two cross-flow filter modules of different pore size that may be used for such purpose. In the FIG. 6 system, the system is correspondingly numbered with respect to FIG. 5 and the same numbered elements are correspondingly constituted, arranged and operated. However, as shown in FIG. 6, the system comprises another cross-flow filter module 83 that is manifolded in parallel flow relationship to filter module 42, with filter module 42 being in branch line 55 containing flow control valve 57 and with the second filter module 83 being coupled to line 40 containing valve 81 and line 89 containing valve 91.

The second filter module 83 is also joined to lines 85 containing valve 87 therein, and line 93, which in turn connects to line 95 containing valves 97 and 99 therein, so that permeate from the second filter module may be selectively drained and/or recirculated to the reservoir 34 as shown, or alternatively so that another mass transfer fluid can be passed in cocurrent flow or A countercurrent flow relationship with the liquid steam being filtered, on an opposite side of the mass transfer element(s) in the cross-flow filter module.

In a specific embodiment of the system having the general arrangement and layout shown in FIG. 6, the filter module 42 may contain filter (membrane) element(s) with an average pore size of 0.04 micron, and the filter module 83 may contain filter (membrane) element(s) with an average pore size of 0.6 micron. It will be recognized that the type and characteristics of the filter element(s) in the filter modules used in the practice of the present invention may be widely varied, as will be readily apparent to those of ordinary skill in the art, and readily implemented with commercially available filter elements suitable for such purpose.

It is important to note that the eluted target substance, e.g., protein or peptide, is desirably captured into a reservoir under appropriate conditions, such as temperature, pH, and salt concentrations. It may be necessary to raise or lower the pH as well as lower the temperature to avoid inactivation or loss of the pure product. For example, immunoglobulins eluted from Protein A resins should be collected in a temperature-controlled reservoir containing Tris buffer, pH 8 at 4° C. to 10° C., which will raise the pH back to neutral and cool the eluate to avoid denaturing the immunoglobulins.

To ready the apparatus for subsequent use, after the target substance is eluted and transferred to the capture reservoir, the elution buffer is switched over to a cleaning buffer, followed by a storage buffer, so that the chromatography resin will be ready for reuse. During this step the permeate is directed to drain.

The eluted target substance, trapped in the capture reservoir, may then be concentrated by means of an additional cross-flow filter module or other appropriate step such as precipitation, freeze drying, evaporation, or centrifugation to remove the elution buffer. In a preferred embodiment, a cross-flow filter module is employed. The filter medium preferably has a pore size smaller than the mean diameter of the target substance and larger than the ions of the elution buffer such that the target substance can be concentrated to an appropriate degree and the contaminating ions removed by diafiltration.

For example, IgG purified and eluted from Protein A resin can be concentrated and diafiltered free of the salts of the elution buffer using a 30,000 molecular weight membrane. Such a cross-filtration module is commercially available from North Carolina SRT, Inc. (Cary, N.C.).

The methods described above have broad utility in purification of target biological substances. The source liquids can be selected from a broad range of materials including serum; plasma and plasma fractions; whole blood; milk; colostrum; whey; bacterial, yeast, fungal, insect or animal cell or tissue culture fluids and tissue homogenates. The target substances can be selected from the extremely broad range of biological substances that are adaptable to filtration purification and that can be selectively or preferentially bound to a chromatography resin, including but not limited to proteins, glycoproteins, hormones, antigens, antibodies, clotting factors, immunoglobulins, and enzymes. The chromatography resins are selected based on the characteristics of the target substance, with a wide range of well-understood ion exchange and affinity ligands being available to the skilled artisan and readily implemented within the skill of the art based on the disclosure and teachings herein.

For example, the method of the invention is useful to purify IgGs from source liquids selected from serum, plasma, plasma fractions, whole blood, milk, colostrum, and whey. Clotting factors can be purified from plasma, whole blood, serum and tissue culture.

The method of the invention has been demonstrated to provide a cost- and time-effective route to purify IgGs from source liquids such as plasma and tissue culture fluids.

A specific aspect of the present invention relates to the processing of a source liquid to recover a purified target substances therefrom, as generally described hereinabove, but wherein the source liquid may include biologically adverse contaminants, e.g., bacterial species, viral species, antigenic species, etc. as contaminants. The invention contemplates the treatment of the source liquid, or other process or product stream in the process, to inactivate such contaminant, and render it non-adverse. By way of example, the contaminant may comprise a viral species, e.g., HIV, hepatitis virus, etc., and the inactivation of same may comprise a viricidal treatment.

The invention in a specific aspect therefore relates to a method of purifying at least one target substance from a source liquid containing a bioactive contaminant, comprising the steps of:

contacting the source liquid with a chromatography resin;
  incubating the source liquid with the chromatography resin for a sufficient contact time to bind to the chromatography resin at least one target substance from the source liquid;
  recirculating the chromatography resin in a cross-flow filter (e.g., one cross-flow filter or more than one cross-flow filter), wherein the following steps are performed:
    concentration and diafiltration of the chromatography resin;
    elution of the target substance from the chromatography resin; and
    separation of the target substance from the chromatography resin by diafiltration;
  recovering the target substance; and
  optionally concentrating the target substance;
  further comprising inactivating the bioactive contaminant during said method.

Such inactivation may involve contacting the bioactive contaminant with an inactivating agent, e.g., as an initial step of the method, or during the incubation of the source liquid with the chromatography resin, during the cross-flow filtration processing (by addition of the inactivating agent to the target-substance containing stream during the filtration operation), or in any other suitable manner. The inactivating agent may be introduced in any suitable form, e.g., as a bound species on a chromatography resin bead that is otherwise functionalized for binding one or more of the target substances, or as a bound species on a bead having only the inactivating agent bound thereto, wherein the inactivating species-bound beads comprise a population component of an overall population of beads including both inactivating species-bound beads and beads functionalized for binding one or more of the target substances.

The inactivation agent for the viral species may be any suitable agent. As used in such context, the term agent is intended to be broadly construed as including any anti-viral molecules, complexation or capture agents which render the viral species non-viable or non-infective, viral transcription inhibitors, viracidal process (exposure) conditions, etc. Specific examples include iodine, chlorine, solvent-detergent compositions, and ultraviolet or other viracidal radiation exposures. Concerning the use of viral capture agents, a viral receptor species may be used to capture the virus in the source liquid. One class of specific viral capture agents includes sialic acids or nonulosaminic acids, as for example N-acetylneuraminic acid, N-glycolylneuraminic acid, $N,O^7$-diacetylneuraminic acid, $N,O^4$-diacetylneuraminic acid, and N,O,O-triacetylneuraminic acid. Accordingly, the chromatographic resin may comprise microbeads with microbead-bound capture agent species, e.g., a microbead functionalized with a sialic acid on its surface.

In a further specific aspect, the invention relates to a process for purifying one or more target substances from a source liquid containing said target substances together with one or more viral species. Such process comprises the following steps:

contacting the source liquid with a viral inactivation agent for the one or more viral species;
  concentrating the target substance(s) in the source liquid by tangential flow filtration in a tangential flow filter comprising a membrane effective to concentrate at least 90% by weight of the target substance(s) in such filtration;
  contacting the source liquid with a chromatography resin;
  incubating the source liquid with the chromatography resin for a sufficient contact time to bind a desired fraction of the target substance(s);
  recirculating the chromatography resin in a cross-flow filter wherein the following steps are performed:
    concentrating the chromatography resin and separating contaminants from the chromatography-resin-bound target substance by diafiltration in a filter comprising a membrane effective to retain the resin and pass species that are not bound to the resin;
    eluting the target substance from the chromatography resin by contact with an elution membrane effective to retain the resin and pass the target substance(s);
    separating the target substance from the chromatography resin by diafiltration;
  recovering the target substance(s); and
  optionally concentrating the target substance(s), e.g., by contact with a concentration membrane effective to yield a concentrate comprising at least 90% by weight target substance(s).

Another process variation within the scope of the invention entails a process for purifying one or more target substances from a source liquid containing such target substances. The process comprises:

contacting the source liquid with a chromatography resin;
  recirculating the chromatography resin in at least one cross-flow filter wherein the following steps are performed:
    concentrating the target substance and chromatography resin in the source liquid by tangential flow filtration;
    diafiltering the chromatography resin in a filter comprising a membrane effective to retain the resin and pass species that are not bound to the resin;
    eluting the target substance from the chromatography resin by contact with an elution membrane effective to retain the resin and pass the target substance(s);
    separating the target substance from the chromatography resin by diafiltration recovering the target substance(s); and
  optionally concentrating the target substance(s).

In the above-described process, the source liquid may contain one or more pathogenic organisms, and the process may in such case further comprise the step of contacting the source liquid with a viral inactivation agent for such one or more pathogenic organisms.

In another aspect and application, the present invention relates to a method of manufacturing universal plasma from blood containing serological Group A and/or Group B antibodies, comprising contacting the blood containing serological Group A and/or Group B antibodies with a chromatography resin comprising corresponding Group A and/or Group B antigen, and recovering an antibodies-depleted blood product as the universal plasma.

The chromatography resin may comprise a microbead of a type as described for example in Schwartz U.S. Pat. No.

4,828,984 issued May 9, 1989 for "Composition, synthesis and use of simulated cells" or Schwartz U.S. Pat. No. 4,774,189 issued Sep. 27, 1988 for "Fluorescent calibration microbeads simulating stained cells," the disclosures of which are hereby incorporated herein by reference in their respective entireties. Schwartz U.S. Pat. No. 4,774,189 describes microbeads functionalized with antigen species, wherein the antigenic species are bound by primary amines on molecules thereof to the microbead through surface epoxy groups on the bead.

The recovery of an antibodies-depleted blood product as the universal plasma in the above-described method may be carried out using various concentration/elution/tangential filtration techniques of the present invention as more specifically described hereinabove.

The features and advantages of the invention are more fully shown with reference to the following non-limiting examples.

EXAMPLE 1

Purification of IgG from Raw Human Plasma

Using the apparatus shown schematically in FIG. 5, IgG was purified from raw human plasma by the method of the invention.

Figure 7:
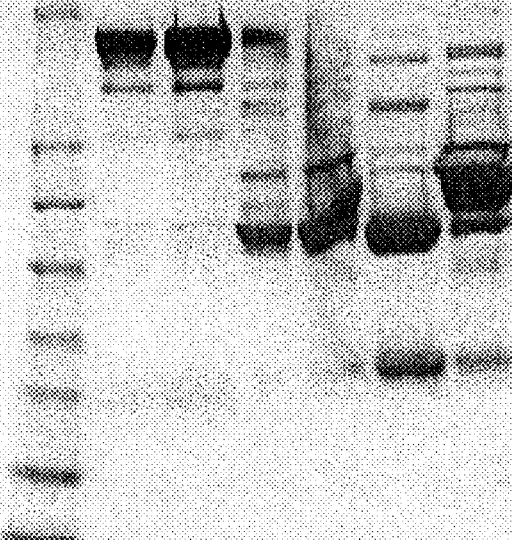
FIG. 7 shows an SDS polyacrylamide gel electrophoresis analysis of an IgG sample purified from raw human plasma by the method of the present invention.

FIG. 7 shows an SDS polyacrylamide gel electrophoresis (SDS-PAGE) performed to evaluate the effectiveness of such purification. Lane 701 is a calibration sample containing several peptides of known molecular weight. Lanes 702 and 703 are 20 μL and 40 μL samples respectively of the sample after five-fold diafiltration by cross-flow chromatography. Lanes 704 and 705 are 20 μL and 40 μL samples respectively of the supernatant of the chromatography resin beads after diafiltration. Lanes 706 and 707 are 40 μL samples of β-mercaptoethanol digests of the materials used in Lanes 702 and 704 respectively.

EXAMPLE 2

Purification of IgG from Tissue Culture Fluid

Using the apparatus shown schematically in FIG. 5, IgG was purified from tissue culture fluid. Tissue culture fluid (20.0 L tissue culture having a concentration of 50 μg/mL IgG) was clarified by filtration using a TRIPORT filter module (North Carolina SRT, Inc., Cary, N.C.). The permeate was directed to a vessel containing a suspension of Orbicell®—Protein A beads (Accurate Polymers, Ltd., Highland Park, Ill.). The suspension of culture fluid and beads was incubated by undergoing total recirculation through the TRIPORT filter module for 15 minutes at ambient temperature. The suspension was concentrated fivefold and then diafiltered ten-fold with 0.4 M NaCl. Elution of the bound IgG was performed by moving the permeate line to a quenching vessel containing a neutralizing buffer and changing the dialysis buffer to an acid elution buffer. The neutralized eluate was concentrated and then diafiltered ten-fold to remove low molecular weight salts formed during acid neutralization. The final yield was approximately 100 mL of purified IgG at a concentration of 10 mg/mL. The total process time was 75 minutes, and the yield of purified IgG was 90–94%.

Figure 8:
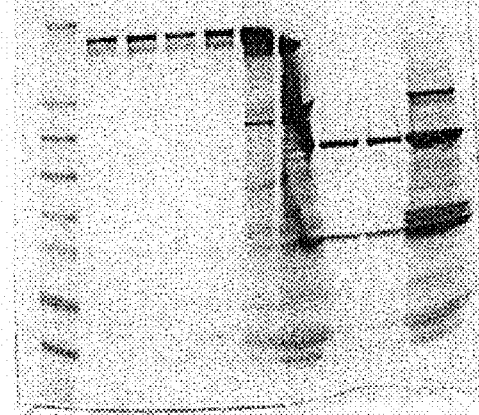
FIG. 8 shows an SDS polyacrylamide gel electrophoresis analysis of an IgG sample purified from cell culture media by the method of the present invention.

FIG. 8 shows an SDS-PAGE analysis performed to evaluate the effectiveness of the above-described purification. Lane 801 is a calibration sample containing several peptides of known molecular weight. Lanes 802 and 803 are 20 μL and 40 μL samples respectively of purified IgG from a first trial of the method of this example. Lanes 804 and 805 are 20 μL and 40 μL samples respectively of purified IgG from a second trial of the method of this example. Lanes 806 and 807 are 20 μL and 40 μL samples respectively of the conditioned media used as starting material in the purification process. Lanes 808 and 809 are 40 μL samples of β-mercaptoethanol digest of the purified IgG from the first and second trials respectively. Lane 810 is a 40 μL sample of a β-mercaptoethanol digest of the conditioned media starting material.

While the invention has been described herein with reference to various illustrative features, aspects and embodiments, it will be appreciated that the invention is susceptable of variations, modifications and other embodiments, other than those specifically shown and described. The invention is therefore to be broadly interpreted and construed as including all such alternative variations, modifications and other embodiments within its spirit and scope as hereinafter claimed.

What is claimed is:

1. A process for purifying one or more target substances from a source liquid, said process comprising:
    contacting the source liquid with a chromatography resin;
    incubating the source liquid with the chromatography resin for a sufficient contact time to allow the resin to bind a desired fraction of one or more target substances,
    recirculating the chromatography resin in a cross-flow filter wherein the following steps are performed:
        concentrating the chromatography resin and separating contaminants from the chromatography-resin-bound target substance by concentration and/or diafiltration;
        eluting the target substance from the chromatography resin; and
        separating the target substance from the chromatography resin by diafiltration;
    recovering the target; and
    optionally concentrating the target substance.

2. The process of claim 1, further comprising an initial clarification of the source liquid.

3. The process of claim 2, wherein the initial clarification is carried out by cross-flow filtration to remove particulate matter.

4. The process of claim 2, wherein the initial clarification is carried out by cross-flow filtration to remove interfering substances.

5. The process of claim 1, wherein the eluted target substance is concentrated and diafiltered in a cross-flow filter module.

6. The process of claim 1, further comprising subjecting permeate generated by the concentration and diafiltration of the chromatography resin, prior to elution, to further purification steps.

7. The process of claim 1, further comprising contacting the eluted target substance with a second chromatography resin for further purification.

8. The process of claim 1, wherein the chromatography resin comprises one or more ligand species selected from the group consisting of: Protein A; Protein A analogs; antibodies; bacterial antigens; viral antigens; and dyes.

9. The process of claim 1, wherein the target substance is an immunoglobulin.

10. The process of claim 1, wherein the source liquid comprises one or more liquids selected from the group consisting of serum, plasma, plasma fractions, whole blood, milk, colostrum, whey, cell fluids, tissue culture fluids, and tissue homogenates.

11. The process of claim 1, wherein the source liquid is selected from the group consisting of plasma, whole blood, serum and tissue culture.

12. The process of claim 1, wherein the target substance is selected from the group consisting of vaccines, clotting factors, immunoglobulins, antigens, antibodies, proteins, glycoproteins, peptides, enzymes.

13. The process of claim 1, wherein the chromatography resin is selected from the group consisting of affinity chromatography resins and ion-exchange resins.

14. The process of claim 1, wherein the chromatography resin comprises an affinity chromatography resin.

15. The process of claim 14, where the affinity chromatography resin comprises rigid, non-porous cellulose beads coupled to affinity ligands.

16. The process of claim 15, wherein the affinity ligands are selected from the group consisting of Protein A and Protein A analogs.

17. A process for purifying an immunoglobulin from a source liquid, said process comprising:
contacting the source liquid with a chromatography resin, wherein the chromatography resin comprises Protein A linked to rigid, non-porous spherical beads;
incubating the source liquid with the chromatography resin for a sufficient contact time to allow the resin to bind a desired fraction of the immunoglobulin;
recirculating the chromatography resin in a cross-flow filter wherein the following steps are performed:
concentrating the chromatography resin and separating contaminants from the chromatography-resin-bound immunoglobulin by diafiltration;
eluting the immunoglobulin from the chromatography resin; and
separating the immunoglobulin from the chromatography resin by diafiltration;
recovering the immunoglobulin; and
optionally concentrating the immunoglobulin.

18. The process of claim 17, wherein the source liquid is selected from the group consisting of tissue culture fluid and raw human plasma.

19. The process of claim 17, wherein the step of incubating the source liquid with the chromatography resin is performed by recirculating the source liquid and chromatography resin between a cross-flow filter module and a reservoir containing the source liquid and chromatography resin.

20. A method of purification of a liquid containing a target substance, comprising the steps of contacting the liquid with a chromatography resin to bind the target substance thereto, and cross-flow filtering the target substance-bound chromatography resin under elution conditions to recover a filtrate comprising the target substance.

21. The method of claim 20, wherein the liquid is clarified prior to said contacting with the chromatography resin.

22. The method of claim 21, wherein said clarification removes contaminants adverse to purification of the liquid.

23. The method of claim 20, wherein said cross-flow filtering comprises diafiltering the target substance-bound chromatography resin against a buffer.

24. The method of claim 20, wherein said cross-flow filtering comprises diafiltering the target substance from the chromatography resin after elution disengagement of the target substance from the chromatography resin.

25. The method of claim 20, wherein the cross-flow filtering produces a permeate and said permeate is further purified.

26. The method of claim 25, wherein further purification of the permeate comprises contacting thereof with a second chromatography resin to bind a selected species of the permeate and cross-flow filtering the selected species-bound second chromatography resin under conditions producing a filtrate containing said selected species as a purification product.

27. The method of claim 20, wherein said filtrate comprising the target substance is further purified.

28. The method of claim 27, wherein further purification of the filtrate comprising the target substance comprises contacting thereof with a second chromatography resin to bind the target substance, and cross-flow filtering the target substance-bound second chromatography resin under elution conditions producing a filtrate containing further purified target substance as a purification product.

29. The method of claim 20, wherein the step of contacting the liquid with a chromatography resin to bind the target substance thereto, comprises adding the liquid to a recirculating loop of chromatography resin using a cross-flow filter prior to imposition of said elution conditions.

30. The method of claim 29, wherein the cross-flow filter is constructed, arranged and operated to discharge permeate liquid at substantially the same rate as said liquid is added for said contacting.

31. The method of claim 20, wherein said contacting of the liquid and the chromatography resin comprises addition of liquid to an agitated constant volume reservoir having chromatographic resin therein.

32. The method of claim 20, wherein said cross-flow filtering is conducted using a cross-flow filter selected from the group consisting of one or more of: hollow fiber filters; spiral filters; plate and frame filters; cassette filters; tubular filters; stirred cells; and ceramic filters.

33. The method of claim 20, wherein the resin has one or more compatible characteristics selected from the group consisting of: spherical shape; irregular shape; porous character; non-porous character; compressible character; and non-compressible character.

34. The method of claim 20, wherein the chromatographic resin comprises at least one ligand selected from the group consisting of: Protein A; antibodies; and antigens.

35. The method of claim 20, carried out to effect a separation selected from the group consisting of:
separating the liquid to produce a vaccine or vaccine component;
separating plasma or a plasma fraction into its constituent parts;
separating clostrum into its constituent parts;
separating milk into its constituent parts;
separating whey into its constituent parts;
separating a fermentation fluid into its constituent parts;
separating insect cell culture fluid into its constituent parts;
separating viral culture fluid into its constituent parts;
separating an immunoglobulin from an immunoglobulin-containing culture of bacteria, yeast, fungus, insect cells, or animal cells;
separating an immunoglobulin from serum;
separating an immunoglobulin from plasma or a plasma fraction;
separating an immunoglobulin from whole blood;
separating an immunoglobulin from milk;
separating an immunoglobulin from clostrum;
separating an immunoglobulin from whey;
separating an immunoglobulin from ascites fluid;

separating a clotting factor from whole blood;
separating a clotting factor from plasma;
separating a clotting factor from serum;
separating a clotting factor from a clotting factor-containing culture of bacteria, yeast, fungus, insect cells, or animal cells;
separating a clotting factor from milk;
separating a clotting factor from whey;
separating a clotting factor from clostrum;
separating a clotting factor from ascites fluid;
separating a protein from a protein-containing culture of bacteria, yeast, fungus, insect cells, or animal cells;
separating an antigen from an antigen-containing culture of bacteria, yeast, fungus, insect cells, or animal cells;
separating an antigen from a viral culture containing same;
separating a hormone from a hormone-containing culture of bacteria, yeast, fungus, insect cells, or animal cells;
separating a hormone from serum;
separating a hormone from plasma or a plasma fraction;
separating a hormone from whole blood;
separating a hormone from plasma;
separating a hormone from serum;
separating a hormone from milk;
separating a hormone from whey;
separating a hormone from clostrum;
separating a hormone from ascites fluid;
separating a hormone from tissue;
separating a glycoprotein from a viral culture;
separating a glycoprotein from a glycoprotein-containing culture of bacteria, yeast, fungus, insect cells, or animal cells;
separating a glycoprotein from serum;
separating a glycoprotein from plasma or a plasma fraction;
separating a glycoprotein from whole blood;
separating a glycoprotein from plasma;
separating a glycoprotein from serum;
separating a glycoprotein from milk;
separating a glycoprotein from whey;
separating a glycoprotein from clostrum;
separating a glycoprotein from ascites fluid; and
separating a glycoprotein from tissue.

36. The method of claim 20, wherein two or more resins are used to purify two or more target substances simultaneously.

37. The method of claim 36, wherein the ligands are antigens and the targets are antibodies.

38. The method of claim 20, wherein the chromatography resin comprises resin particles, wherein at least some of the resin particles have multiple ligands thereon, whereby different target substances may be bound by a single resin particle.

39. A method of separating a liquid in a separation system comprising a bioreactor, a chromatographic resin reservoir, a first cross-flow filtration module, a second cross-flow filtration module, and a third cross-flow filtration module, said method comprising clarifying the perfusate of the bioreactor in the first cross-flow filtration module to yield a permeate, flowing the permeate to the chromatographic resin reservoir and flowing chromatographic resin and permeate to the second cross-flow filtration module for concentration, diafiltration and elution to yield an eluate, and flowing the eluate to the third cross-flow filtration module for concentration and diafiltration therein.

40. The method of claim 39, wherein said bioreactor is of a type selected from the group consisting of hollow fiber bioreactors and cell culture bioreactors.

41. A method of purifying at least one target substance from a source liquid containing a bioactive contaminant, comprising the steps of:
    contacting the source liquid with a chromatography resin;
    incubating the source liquid with the chromatography resin for a sufficient contact time to bind to the chromatography resin at least one target substance from the source liquid;
    recirculating the chromatography resin in a cross-flow filter wherein the following steps are performed:
        concentration and diafiltration of the chromatography resin;
        elution of the target substance from the chromatography resin; and
        separation of the target substance from the chromatography resin by diafiltration;
    recovering the target substance; and
    optionally concentrating the target substance;
    further comprising inactivating the bioactive contaminant during said method.

42. The method of claim 41, wherein the bioactive contaminant comprises a bioactive species selected from the group consisting of bacteria, yeasts, viruses and immunoantigens.

43. The method of claim 41, wherein the bioactive contaminant comprises a virus.

44. The method of claim 41, wherein the bioactive contaminant comprises HIV.

45. The method of claim 41, wherein said inactivation comprises contacting the bioactive contaminant with an inactivating agent.

46. The method of claim 45, wherein said inactivating agent comprises a microbead-bound inactivating agent species.

47. The method of claim 45, wherein said inactivating agent comprises a microbead-bound capture agent for the bioactive contaminant.

48. The method of claim 45, wherein said inactivating agent comprises radiation.

49. The method of claim 45, wherein said inactivating agent comprises an agent selected from the group consisting of iodine, chlorine, solvent-detergent compositions, and ultraviolet radiation.

50. The method of claim 41, wherein said inactivation comprises contacting the bioactive contaminant with an inactivating agent as an initial step of the method.

51. The method of claim 41, wherein said inactivation comprises contacting the bioactive contaminant with an inactivating agent during the incubation of the source liquid with the chromatography resin.

52. The method of claim 41, wherein said inactivation comprises contacting the bioactive contaminant with an inactivating agent during cross-flow filtration processing.

53. A process for purifying one or more target substances from a source liquid containing said target substances together with one or more viral species, such process comprising:
    contacting the source liquid with a viral inactivation agent for the one or more viral species;

concentrating the target substance(s) in the source liquid by tangential flow filtration in a tangential flow filter comprising a membrane effective to concentrate at least 90% by weight of the target substance(s) in such filtration;

contacting the source liquid with a chromatography resin;

incubating the source liquid with the chromatography resin for a sufficient contact time to bind a desired fraction of the target substance(s);

recirculating the chromatography resin in a cross-flow filter wherein the following steps are performed:

concentrating the chromatography resin and separating contaminants from the chromatography-resin-bound target substance by diafiltration in a filter comprising a membrane effective to retain the resin and pass species that are not bound to the resin;

eluting the target substance from the chromatography resin by contact with an elution membrane effective to retain the resin and pass the target substance(s);

separating the target substance from the chromatography resin by diafiltration;

recovering the target substance(s); and optionally concentrating the target substance(s).

54. A process for purifying one or more target substances from a source liquid containing said target substances, such process comprising:

contacting the source liquid with a chromatography resin;

recirculating the chromatography resin in at least one cross-flow filter wherein the following steps are performed:

concentrating the target substance and chromatography resin in the source liquid by tangential flow filtration;

diafiltering the chromatography resin in a filter comprising a membrane effective to retain the resin and pass species that are not bound to the resin;

eluting the target substance from the chromatography resin by contact with an elution membrane effective to retain the resin and pass the target substance(s);

separating the target substance from the chromatography resin by diafiltration recovering the target substance(s); and optionally concentrating the target substance(s).

55. The process of claim 54, wherein the source liquid contains one or more pathogenic organisms, further comprising contacting the source liquid with a viral inactivation agent for the one or more pathogenic organisms.

56. The process of claim 54, comprising concentrating the target substance(s) by contact with a concentration membrane effective to yield a concentrate comprising at least 90% by weight target substance(s).

57. The method of claim 54, wherein the chromatography resin comprises microbeads.

58. The method of claim 54, wherein said microbeads have surface epoxy functionality, and said microbeads are functionalized with antigen species bound by primary amines on molecules thereof to the microbead through said surface epoxy functionality on the bead.

59. A method of manufacturing universal plasma from blood containing serological Group A and/or Group B antibodies, comprising contacting the blood containing serological Group A and/or Group B antibodies with a chromatography resin comprising corresponding Group A and/or Group B antigen, and recovering an antibodies-depleted blood product as the universal plasma.

60. A process for purifying a target substance from a source liquid, including the steps of contacting the source liquid with a chromatography resin having affinity for said target substance, to bind said target substance to the chromatography resin; and cross-flow filtering the chromatography resin to recover said target substance from the chromatography resin.

61. The process of claim 60, wherein the source liquid comprises serum, plasma, a plasma fraction, whole blood, milk, colostrum, whey, a cell fluid, tissue culture fluid, or tissue homogenate.

62. The process of claim 60, wherein said target substance comprises a vaccine, a clotting factor, an immunoglobulin, an antigen, an antibody, a protein, a glycoprotein, a peptide or an enzyme.

* * * * *

UNITED STATES PATENT AND TRADEMARK OFFICE
CERTIFICATE OF CORRECTION

PATENT NO.     : 6,139,746
DATED          : October 31, 2000
INVENTOR(S)    : Henry B. Kopf It is certified that error appears in the above-identified patent and that said Letters Patent is hereby corrected as shown below:

Column 9,
Line 39, change "impertpeate" to -- impermeate --.
Line 67, change "group s" to -- groups --.

Signed and Sealed this

Twenty-first Day of January, 2003

JAMES E. ROGAN
*Director of the United States Patent and Trademark Office*